(12) United States Patent
Karoum et al.

(10) Patent No.: US 9,671,381 B2
(45) Date of Patent: Jun. 6, 2017

(54) DEVICE FOR ANALYZING AT LEAST ONE HYDROCARBON CONTAINED IN A DRILLING FLUID AND ASSOCIATED METHOD

(75) Inventors: Reda Karoum, Thiais (FR); Jerome Breviere, Taverny (FR); Patrick Banik, Paris Nord II (FR)

(73) Assignee: GEOSERVICES EQUIPEMENTS, Roissy en France (FR)

(*) Notice: Subject to any disclaimer, the term of this patent is extended or adjusted under 35 U.S.C. 154(b) by 793 days.

(21) Appl. No.: 13/880,978

(22) PCT Filed: Oct. 20, 2011

(86) PCT No.: PCT/IB2011/054699
§ 371 (c)(1),
(2), (4) Date: May 23, 2013

(87) PCT Pub. No.: WO2012/052962
PCT Pub. Date: Apr. 26, 2012

(65) Prior Publication Data
US 2013/0233057 A1    Sep. 12, 2013

Related U.S. Application Data

(60) Provisional application No. 61/407,589, filed on Oct. 28, 2010.

(30) Foreign Application Priority Data

Oct. 22, 2010    (EP) .................................... 10306151

(51) Int. Cl.
*G01N 21/72* (2006.01)
*G01N 33/00* (2006.01)
(Continued)

(52) U.S. Cl.
CPC ......... *G01N 33/0013* (2013.01); *B01D 53/22* (2013.01); *G01N 1/2294* (2013.01);
(Continued)

(58) Field of Classification Search
CPC .. E21B 49/10; E21B 47/00; G01J 2003/1213; G01J 3/108; G01J 3/26; G01N 21/031;
(Continued)

(56) References Cited

U.S. PATENT DOCUMENTS 3,666,824 A   5/1972  Jenkins
5,473,162 A * 12/1995 Busch et al. ............... 250/341.6
(Continued)

FOREIGN PATENT DOCUMENTS

CN    101427114    5/2009
GB      2372040    8/2002
(Continued)

OTHER PUBLICATIONS

Office action for the equivalent Chinese patent application No. 201180056912.5 issued on Jun. 11, 2014.
(Continued)

*Primary Examiner* — Hezron E Williams
*Assistant Examiner* — Gedeon M Kidanu
(74) *Attorney, Agent, or Firm* — Michael Dae

(57) ABSTRACT

The device comprises an extractor (53) having an outlet (71) at which a gas stream is sampled. The gas stream contains at least one hydrocarbon to be analyzed and at least one interfering compound. A transport line (54), is connected to the outlet (71) of the extractor (53) to transport the gas stream to an analyzer (55A) comprising a detector being able to measure at least one of the hydrocarbons to be analyzed contained in this gas stream. The device comprises a chemical reactor (141) located between the extractor (53) and the detector. At least a portion of the extracted gases is
(Continued)

transported through the chemical reactor (141) where a selective catalytic reaction of at least one interfering compound is carried out without any substantial reaction of at least one of the hydrocarbons to be analyzed.

19 Claims, 4 Drawing Sheets

(51) Int. Cl.
| | |
|---|---|
| *B01D 53/22* | (2006.01) |
| *G01N 1/22* | (2006.01) |
| *G01N 1/40* | (2006.01) |
| *G01N 30/88* | (2006.01) |
| *G01N 33/28* | (2006.01) |
| *G01N 1/20* | (2006.01) |
| *G01N 30/02* | (2006.01) |
| *G01N 30/06* | (2006.01) |

(52) U.S. Cl.
CPC .......... *G01N 1/4044* (2013.01); *G01N 21/72* (2013.01); *G01N 30/88* (2013.01); *G01N 33/2823* (2013.01); *C10G 2300/1033* (2013.01); *G01N 1/2035* (2013.01); *G01N 2030/025* (2013.01); *G01N 2030/067* (2013.01); *G01N 2030/8854* (2013.01); *G01N 2030/8868* (2013.01)

(58) Field of Classification Search
CPC ..... G01N 21/3504; G01N 2201/06186; G01N 33/2823; G01N 21/59; G01N 33/28; G02B 26/02; B01D 53/22; C10G 2300/1033
USPC .......... 73/31, 863; 175/50; 702/6, 9, 24, 25; 422/68, 83; 507/101, 103, 116, 203
See application file for complete search history.

(56) References Cited

U.S. PATENT DOCUMENTS

| | | | | |
|---|---|---|---|---|
| 6,443,001 | B1* | 9/2002 | Duriez et al. | 73/152.19 |
| 7,094,736 | B2* | 8/2006 | Jones et al. | 507/103 |
| 7,408,645 | B2* | 8/2008 | DiFoggio | 356/436 |
| 7,748,266 | B2* | 7/2010 | Evrard et al. | 73/152.23 |
| 7,779,667 | B2* | 8/2010 | Evrard | 73/19.09 |
| 8,448,495 | B2* | 5/2013 | Breviere et al. | 73/31.05 |
| 8,616,051 | B2* | 12/2013 | Kimour et al. | 73/152.04 |
| 2003/0049855 | A1 | 3/2003 | Rhodes | |
| 2006/0224333 | A1* | 10/2006 | Frechin et al. | 702/24 |
| 2009/0293605 | A1* | 12/2009 | Evrard et al. | 73/152.25 |
| 2010/0031732 | A1* | 2/2010 | Breviere et al. | 73/23.37 |
| 2010/0162791 | A1* | 7/2010 | Breviere et al. | 73/23.31 |
| 2011/0000294 | A1* | 1/2011 | Kimour | B01D 53/0423 73/152.04 |
| 2011/0094736 | A1* | 4/2011 | Evrard | 166/267 |
| 2011/0123423 | A1* | 5/2011 | Ciambelli et al. | 423/245.1 |
| 2011/0303463 | A1* | 12/2011 | Lessi | 175/50 |
| 2013/0233057 | A1* | 9/2013 | Karoum et al. | 73/31.07 |

FOREIGN PATENT DOCUMENTS

| | | | | |
|---|---|---|---|---|
| WO | 2008/017949 | 2/2008 | | |
| WO | WO 2008017949 A1 * | 2/2008 | | G01N 1/2294 |
| WO | 2009/037517 | 3/2009 | | |
| WO | 2009/090351 | 7/2009 | | |
| WO | WO 2009090351 A1 * | 7/2009 | | B01D 53/0423 |

OTHER PUBLICATIONS

L.M. Wenger, et al, "Drill-bit metamorphism: Recognition and impact on show evaluation," Proceedings—SPE Annual Technical Conference and Exhibition—Society of Petroleum Engineers—2009, ATCE 2009, vol. 7, pp. 4565-4573.

* cited by examiner

DEVICE FOR ANALYZING AT LEAST ONE HYDROCARBON CONTAINED IN A DRILLING FLUID AND ASSOCIATED METHOD

The present invention relates to a device for analyzing at least one hydrocarbon contained in a drilling fluid, comprising:
- an extractor for continuously extracting gases contained in the drilling fluid, the extractor having an outlet at which the gas stream is sampled, the gas stream containing at least one hydrocarbon to be analyzed and at least one interfering compound;
- a transport line, connected to the outlet of the extractor to transport the gas stream;
- an analyzer comprising a detector able to measure the hydrocarbons to be analyzed in the gas stream.

During the drilling process of an oil well or of a well of another effluent (in particular gas, vapour, water), it is known to carry out an analysis of the gaseous compounds contained in the drilling fluids (generally referred to as drilling muds) emerging from the well. Such an analysis makes possible the reconstruction of geological sequences which are passed through during the drilling operations, and plays a part in determining the possibilities of exploiting the deposits of fluids encountered.

While drilling, chemical analyses are performed continuously and comprise two main steps. The first analysis consists in extracting the gases carried by the drilling mud (for example hydrocarbons, carbon dioxide, hydrogen sulphide . . . ), whereas the second one consists in qualifying and quantifying the extracted gases.

For the first step, mechanically agitated degassers of the aforementioned type (FR-A-2 799 790) are frequently used. The gases extracted from the drilling mud, which are mixed with a carrier gas introduced into the enclosure, are conveyed by suction via the gas extraction pipe to an analyzer permitting a quantification of these extracted gases.

To this end, the analyzer may comprise a separation column for separating the different components to be analyzed according to their elution time in the column, and at least one detector associated with suitable calculation to qualify and/or quantify each component to be analyzed.

When drilling an oil well, it is known for example to analyze and to quantify in such a way the $C_1$ to $C_5$ hydrocarbons. In some cases, it is also possible to determine the presence of any $C_6$ to $C_8$ hydrocarbons from the extracted sample.

Additionally, or in a variant, the isotopic ratio $^{12}C/^{13}C$ of a particular hydrocarbon, such as methane, ethane or propane may also be determined.

These analyses are sometimes not entirely satisfactory because of the presence of pollutant compounds interfering with the analysis method described.

These pollutant compounds (or interfering components) can be present in particular when specific drilling muds, such as synthetic oils, are used. Indeed, these drilling fluids are liable to contain interfering compounds having an elution time which occurs between the elution time of the first hydrocarbon to be analyzed and the elution time of the last one to be analyzed. These interfering compounds are present by nature in the constituents of the drilling muds, or are the results of chemical reactions between compounds contained in the drilling muds. Such reactions occur when the mud is exposed to the high temperatures and pressures encountered at the bottom of the well.

In the case of isotopic analysis of methane, known interfering compounds, such as ethylene ($C_2H_4$), can skew the isotopic measurement of methane, although ethylene is not a compound originating from the formation gases, but results from complex drilling processes known as Drill Bit Metamorphism.

In order to overcome this problem, WO 2009/090351 discloses an analyzing device including a surface having a chemical and/or physical interaction with the interfering compounds, which is able to selectively retain the interfering compounds and not the hydrocarbons to be analyzed. The surface is for example defined in a removable cartridge which is placed on the transport line, or in a pre-cut column which is located before the analysis device.

In the analysis method disclosed in WO 2009/090351, the interfering compounds are therefore extracted out of the gas stream containing the hydrocarbons to be analyzed and retained on the interaction surface.

Hence, the method is extremely efficient to obtain an accurate analysis of the hydrocarbons gases extracted from the drilling muds. However, after some time, the interaction surface may be completely saturated with interfering compounds. That is why the surface must be removed or regenerated to maintain the efficiency of the method.

An object of the invention is to provide a device allowing an on-line analysis of at least one or of a plurality of hydrocarbons contained in a drilling fluid in a very accurate manner, the device being easy to operate, with a minimal maintenance.

To this end, the invention relates to a device of the aforementioned type, characterized by a chemical reactor located between the extractor and the detector and receiving at least part of the gas stream, the chemical reactor being able to carry out a selective catalytic reaction of at least one interfering compound present in the gas stream without any substantial reaction of at least one of the hydrocarbons to be analyzed.

The device according to the invention may comprise one or more of the following features, taken in isolation or in any technically possible combination(s):
- the device comprises a temperature control unit to control the temperature of the selective catalytic reaction of the at least one interfering compound in the chemical reactor;
- the chemical reactor comprises a UV light unit able to carry out a selective photo-oxidation of the at least one interfering compound;
- the chemical reactor contains a catalytic system, in particular a catalyst, such as platinum particles, dispersed on a support, such as an oxide;
- the catalyst comprises at least a metal, advantageously a transition metal such as platinum, rhodium or palladium;
- the device comprises a separation column, able to separate a plurality of hydrocarbons to be analyzed according to their elution time in the separation column, the separation column being placed between the extractor and the detector, upstream or downstream of the chemical reactor;
- the analyzer comprises a compositional analysis unit, comprising calculation means suitable for qualifying and/or quantifying each hydrocarbon to be analyzed; and
- the analyzer comprises an isotopic measurement unit.

The invention further relates to a method for analyzing at least one hydrocarbon contained in a drilling fluid, comprising the following steps:

continuously extracting a gas stream of gases contained in the drilling fluid within an extractor, at an outlet of the extractor, sampling the gas stream where at least one hydrocarbon to be analyzed and at least one interfering compound are present;

collecting and transporting the gas stream through a transport line connected to the outlet of the extractor;

measuring at least one of the hydrocarbons to be analyzed in the gas stream in an analyzer comprising a detector;

characterized in that the method comprises:

passing at least part of the gas stream through a chemical reactor located between the extractor and the detector;

carrying out a selective catalytic reaction of at least one of the interfering compounds in the chemical reactor, without any substantial reaction of at least one of the hydrocarbons to be analyzed.

The method according to the invention may comprise one or more of the following characteristics, taken in isolation or in any technically possible combination(s):

the selective reaction step comprises substantially reacting at least 85 molar percent of the interfering compounds, without substantially reacting at least 85 molar percent of the hydrocarbon to be analyzed;

the selective reaction step comprises controlling the temperature of the chemical reactor in a temperature range where at least one of the interfering compounds selectively reacts, without any substantial reaction of at least one of the hydrocarbons to be analyzed;

the selective reaction step comprises selectively oxidizing, in particular photo-oxidizing, at least one of the interfering compounds in the chemical reactor without substantially oxidizing at least one of the hydrocarbons to be analyzed;

the method comprises a step of passing the gas stream into a separation column connected to the transport line in order to separate a plurality of hydrocarbons to be analyzed according to their elution time in the separation column;

the analyzing step comprises qualifying and/or quantifying each hydrocarbons to be analyzed; and the analyzing step comprises the determination of the isotopic content of at least one of the hydrocarbons to be analyzed.

The invention will be better understood upon reading the following description, which is given solely by way of example, and which is written with reference to the appended drawings, in which.

In everything which follows, the terms "upstream" and "downstream" are understood with respect to the normal direction of circulation of a fluid in a pipe.

An analysis device according to the invention is used for example in a drilling installation 11 for a fluid production well, such as a hydrocarbon production well.

Figure 1:
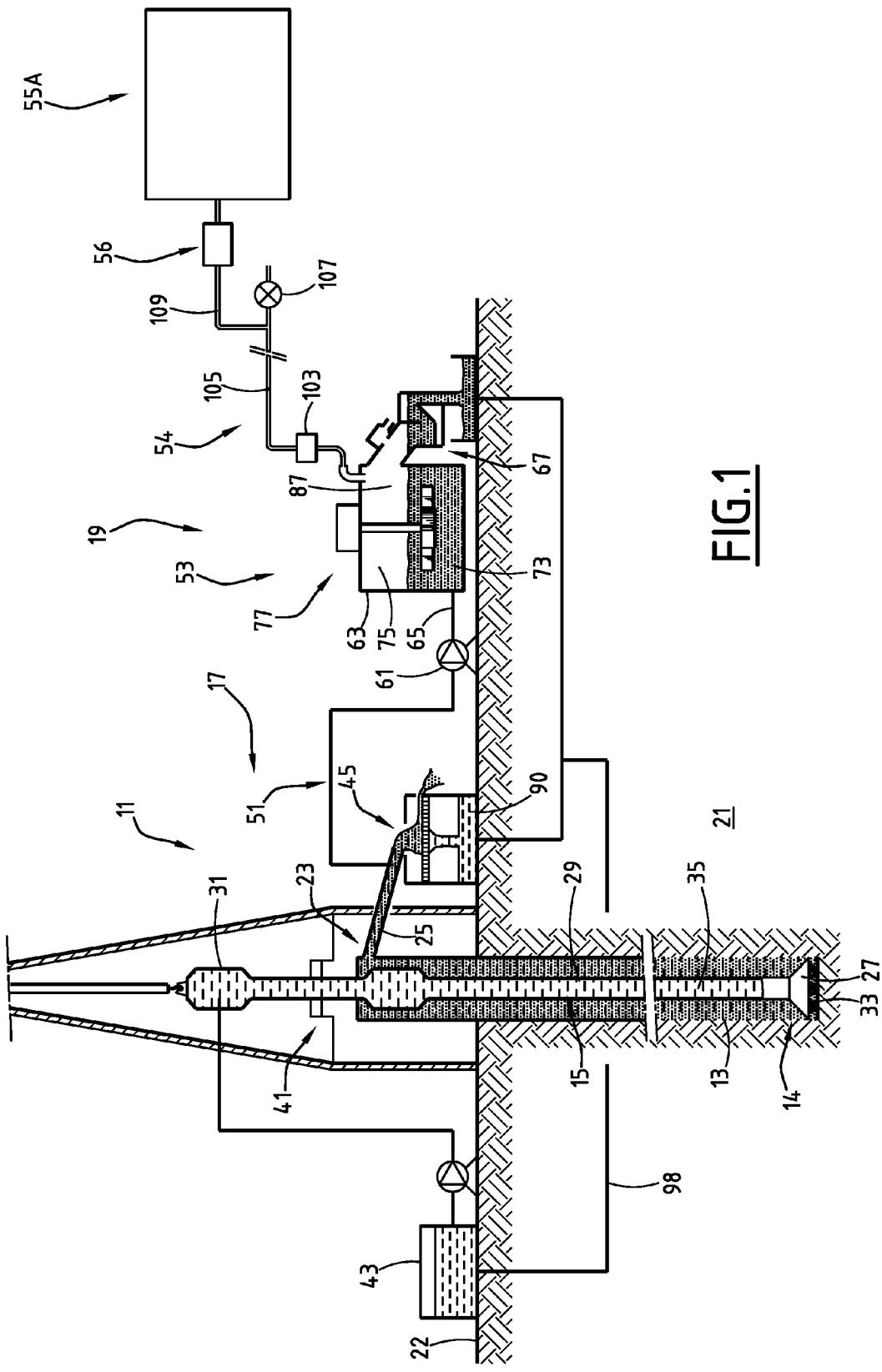
FIG. 1 is a schematic view, in vertical section, of a drilling installation provided with a first analysis device according to the invention.

As illustrated in FIG. 1, this installation 11 comprises a rotary drilling tool 15 drilling a cavity 14, a surface installation 17, where drilling pipes are placed in the cavity 14 and a first analysis device 19 according to the invention.

The borehole 13 delimiting the cavity 14 is formed in the substratum 21 by the rotary drilling tool 15. At the surface 22, a well head 23 having a discharge pipe 25 closes the borehole 13.

The drilling tool 15 comprises a drilling head 27, a drill string 29 and a liquid injection head 31.

The drilling head 27 comprises means 33 for drilling through the rocks of the substratum 21. It is mounted on the lower portion of the drill string 29 and is positioned in the bottom of the drilling pipe 13.

The drill string 29 comprises a set of hollow drilling pipes. These pipes delimit an internal space 35 which makes it possible to bring a drilling fluid from the surface 22 to the drilling head 27. To this end, the liquid injection head 31 is screwed onto the upper portion of the drill string 29.

The drilling fluid is in particular a drilling mud, in particular a water-based or oil-based drilling mud.

The surface installation 17 comprises means 41 for supporting the drilling tool 15 and driving it in rotation, means 43 for injecting the drilling liquid and a shale shaker 45.

The injection means 43 are hydraulically connected to the injection head 31 in order to introduce and circulate the drilling fluid in the inner space 35 of the drill string 29.

The shale shaker 45 collects the drilling fluid charged with drilling residues (cuttings) which flow out from the discharge pipe 25. The shale shaker equipped with sieves allows the separation of the solid drilling residues (cuttings) from the drilling mud.

Figure 2:
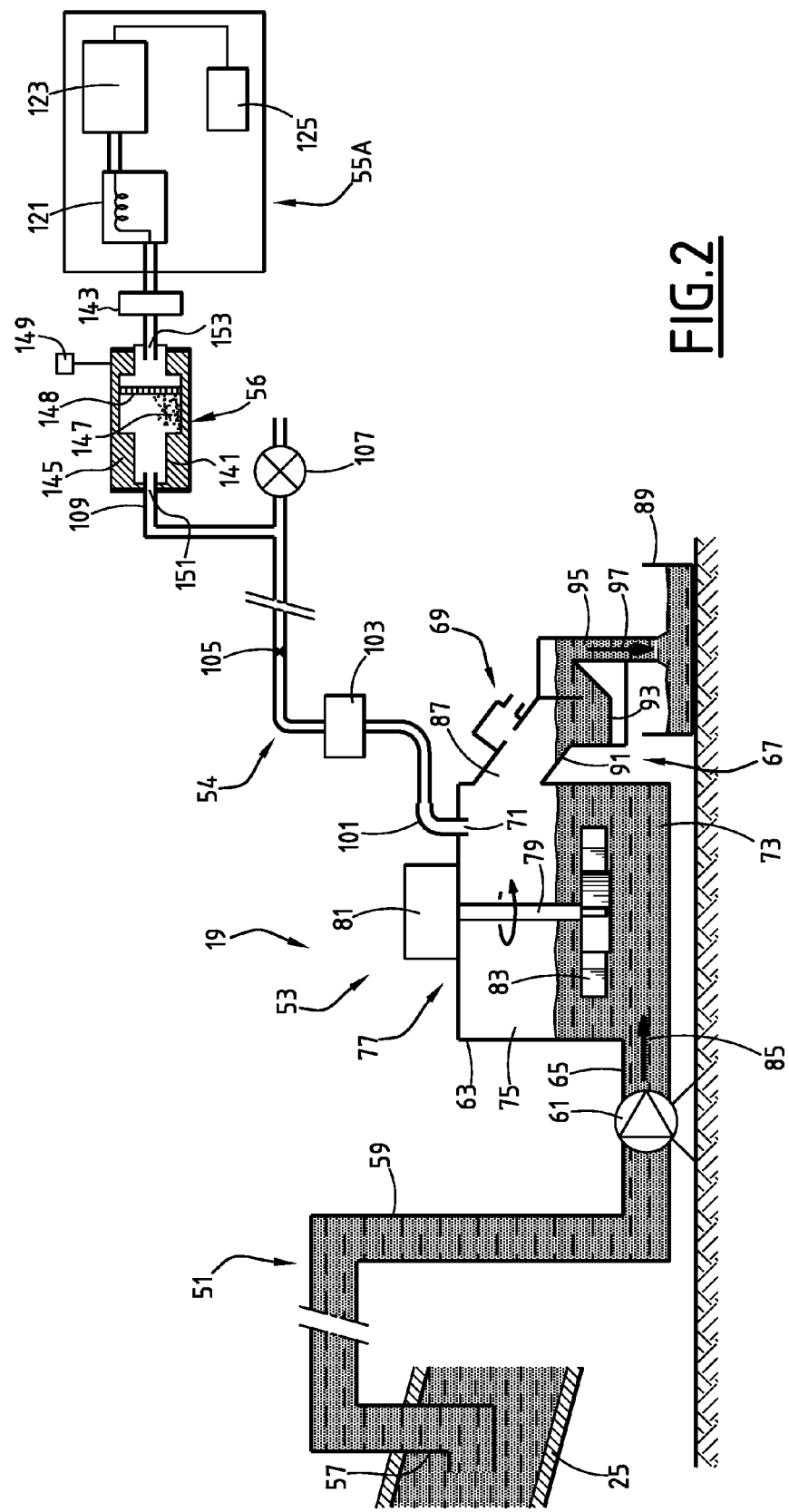
FIG. 2 is a schematic view, in vertical section, of the main elements of the first analysis device according to the invention.

As illustrated in FIG. 2, the analysis device 19 comprises means 51 for sampling the mud, which in this example, are tapped into the discharge pipe 25, a gas extractor 53 and a line 54, the line 54 allowing the transport of the extracted gases from the extractor 53 to the analytical device 55A.

The analysis device 19 further comprises an analyzer 55A for the extracted gases, connected to the transport line 54, and, in accordance with the invention, means 56 for selectively treating the gases extracted from the drilling fluid, before being analyzed. In the embodiment of FIG. 1, the treatment means 56 are mounted in series on the transport line 54 between the extractor 53 and the analyzer 55A.

The sampling means 51 comprise a liquid sampling device 57, connected to the discharge pipe 25, a connecting tube 59 and a peristaltic pump 61 with an adjustable flow rate.

In a variant, the sampling means 51 are installed in a receiving tank for the liquid flowing out from the discharge pipe 25, e.g. in the vicinity of the shale shaker 45. In another variant, the sampling means 51 are located in a tank directly connected to the mud injection means 43.

In the example shown in FIG. 2, the extractor 53 comprises an enclosure 63, a pipe 65 for supplying mud into the enclosure 63, a pipe 67 for evacuating the mud from the enclosure 63, an inlet 69 for introducing a carrier gas into the enclosure 63 and an outlet 71 for extracting the extracted gases from the enclosure 63.

The enclosure 63 comprises a hermetic receptacle, with an internal volume which is for example between 0.4 liters and 3 liters. This enclosure 63 comprises a lower portion 73, where the mud circulates, and an upper portion 75, free of mud. The enclosure 63 is further provided with agitating means 77, comprising an agitator 79, installed into the enclosure 63 and driven in rotation by a motor 81 mounted on the upper portion 75 of the enclosure 63. The agitator 79 comprises an agitating mechanism 83 immersed in the mud.

The mud supply pipe 65 extends between the outlet of the peristaltic pump 61 and an entry opening 85, formed in the lower portion 73 or upper portion 75 of the enclosure 63.

This supply pipe 65 may be provided with means for heating the mud (not shown), in order to bring the temperature of the mud to values between 5° C. and 150° C., preferably between 60° C. and 90° C.

The evacuation pipe 67 extends between an overflow passage 87, formed in the upper portion 75 of the enclosure 63, and a retention tank 89 for receiving the mud evacuated from the device 53.

In a variant, the retention tank 89 is formed by a receiving tank 90 for the liquids extracted from the shale shaker 45, shown in FIG. 1.

In this example, the evacuation pipe 67 comprises in succession an upstream portion 91 inclined downwards, which is at an angle e.g. of approximately 45° C. to the horizontal, an angled portion 93 forming a siphon, and a substantially vertical downstream portion 95, open at its lower end 97 arranged facing the tank 89, above the level of the liquid contained in the tank 89.

The mud collected in the retention tank 89 and in the tank 90 is recycled to the injection means 43 by a mud recirculation pipe 98.

The introduction inlet 69 opens into the upper portion 75 of the enclosure 63. It is advantageously connected to a source (not shown) of a carrier gas such as air, nitrogen or helium. In a variant, the inlet 69 opens into the atmosphere located around the enclosure 63.

The outlet for evacuating the extracted gases 71 is delimited in an upper portion of the enclosure, advantageously in the vicinity of the agitator 75. It comprises a fitting 101 for connection to the transport line 54.

The line 54 is mounted on the fitting 101. The line 54 is capable of continuously sampling a stream of extracted gases from the mud in the upper portion 75 of the enclosure 63 in order to convey this gas stream to the analyser 55A.

As it will be seen below, this gas stream contains mostly carrier gas, hydrocarbons to be analyzed, water vapour, and pollutants (or interfering compounds).

The upstream gas stream, before entering the treatment means 56, contains at least one compound other than water, which can interfere with the analysis of at least one hydrocarbon. The interfering compounds referred to here will be defined more precisely below.

The analyzed hydrocarbons are for example $C_1$ to $C_n$ hydrocarbons, with n being less than or equal to 10, advantageously with n being less than or equal to 8.

As will be seen further below, the interfering compounds other than water will depend on the nature of the drilling mud used and the drilling conditions. The interfering compounds may also depend on the nature of the analyzer devices which are used.

In one example, the interfering compound is an unsaturated hydrocarbon which interferes with the measurement of the methane contained in the gas stream. In one particular example, the interfering compound is a linear, branched, or cyclic unsaturated hydrocarbon having a number of carbons atoms lower than 6, advantageously lower than 4.

In one particular example, the interfering compound is ethylene. In another example, the interfering compounds comprise at least one heteroatom, in particular an oxygen, nitrogen or sulphur atom.

In particular, these interfering compounds further include a $C_1$ to $C_{10}$ hydrocarbon group, in particular a $C_1$ to $C_5$ hydrocarbon group which may be linear, branched or cyclic, either saturated or unsaturated. They include for example a $C_1$ to $C_{10}$ alkyl or alkene or alkyne group substituted by one or more —OH, —NH$_2$, —NH—R$_1$, —NR$_2$R$_3$, —OR$_4$, —SH, —SR$_5$, —R$_6$COO(R$_7$) group(s) in which R$_1$ to R$_7$, independently of one another, represent $C_1$ to $C_{10}$ alkyl groups.

The interfering compounds are in particular alcohols, ethers or esters which have a number of carbon atoms of less than 10, in particular a number of carbon atoms of less than 5.

In another example, the interfering compound is ammonia (NH$_3$).

In reference to FIG. 2, the transport line 54 connects the enclosure 63 arranged in the vicinity of the well head 23, in the explosive zone, to the analyzer 55A, which is located further away from the well head 23, in a non-explosive zone, for example in a pressurised unit. In a variant, the line 54 is very short and the analyser 55A is placed in the explosive zone in the vicinity of the well head.

The transport line 54 is preferably manufactured with a material which is inert towards the gaseous compounds extracted from the mud, such as steel, polyethylene (PE), perfluoroethylene (FEP) or PTFE. The length of the transport line 54 varies for example between 10 cm and 500 m.

The transport line 54 is equipped, from upstream to downstream in FIG. 2, with a water trap 103, a flow rate controller 105 located in the vicinity of the enclosure 63, a vacuum pump 107 intended to convey the extracted gases, and a branch connection 109 to connect the analyzer 55A upstream from the pump 107.

The water trap 103 comprises at least one cold water condensation surface in order to eliminate the water vapour present in the extracted gases substantially by condensation.

The flow rate controller 105 is formed for example by a tube having a constriction of calibrated cross-section. The controller sets a volumetric flow rate for extracted gases stream which circulates in the line 54. This flow rate is for example of between 100 mL per minute and 2000 mL per minute, and advantageously equal to 500 mL per minute.

The pump 107 permits the transport of the extracted gases from the enclosure 63 to the analyzer 55A by suction. It is placed in the vicinity of the analyzer 55A. It has an inlet connected to the line 54 in parallel to the branch connection 109 and an evacuation outlet which opens into the atmosphere.

The branch connection 109 opens upstream from the pump 107. It is capable of sampling up to 20% of the volume flow rate of extracted gases circulating in the line 54, while the rest of the flow of extracted gases circulating through the pump 107 is evacuated into the atmosphere.

In the example of FIG. 2, the analyzer 55A comprises a separation column 121 for the hydrocarbons to be analyzed, a detector 123 for successive detection of each hydrocarbon circulating in the separation column 121, and means 125 for qualification and/or quantification of the hydrocarbons that have been identified by the detector 123.

The separation column 121 is a gas-chromatography separation column. This column is for example charged with a stationary phase in the form of a gel which allows the selective dissolution of the hydrocarbons in the gel in order to retain them selectively (gas-liquid chromatography). In a variant, the column has a solid coating allowing an interaction with the hydrocarbons to be analyzed in order to retain them selectively according to their specific affinities with the coating phase (gas-solid chromatography).

The separation column 121 is capable of successively eluting the hydrocarbons to be analyzed according to their number of carbons (from $C_1$ to $C_n$) from a gas stream injected at the inlet of the analyzer 55A. The hydrocarbons to be analyzed emerge from the column 121 with distinct elution times occurring between 10 s and 150 s.

In the context of the present invention, and in everything which follows, "interfering compounds" would have an elution time in the separation column 121 between the elution time of the first hydrocarbon to be analyzed, namely $C_1$ hydrocarbon, and the elution time of the last hydrocarbon to be analyzed, namely $C_n$ hydrocarbon, if these interfering compounds had been injected into the column 121 at the same time than the hydrocarbons to be analyzed.

The detector 123 is for example a flame ionisation detector (FID), or alternatively a thermal conductivity detector (TCD), or alternatively a mass spectrometer (MS), depending on the type of analysis wanted.

The qualification and/or quantification means 125 are capable of qualifying and/or quantifying the $C_1$ to $C_n$ hydrocarbons with n being less than or equal to 10, advantageously with n being less than or equal to 8, in order to detect their presence in the gas stream, and to quantify their relative contents.

According to the invention, the treatment means 56 comprise a chemical reactor 141, and a collector 143, located downstream of the reactor 141, to carry out the selective reaction of at least one interfering compound and advantageously collect at least one product of the reaction with the interfering compound.

By "selective reaction of the interfering compound" it is meant that at least one interfering compound substantially and independently reacts in the chemical reactor 141 whereas no substantial reaction with at least one hydrocarbon to be analyzed occurs.

The chemical reactor 141 is made for example of a duct. This duct, where the untreated gas stream containing the hydrocarbons to be analyzed has to pass through, could be a glass, or ceramic or steel tube containing a catalytic system 147 to induce the desired reaction in the reactor 141.

In an embodiment, the treatment means 56 further comprise a furnace 145 and a temperature control unit 149 to allow the adjustment and optimisation of the temperatures of desired reactions. The chemical reactor 141 is advantageously a tubular fixed bed reactor.

In this example, the treatment means 56 which include the chemical reactor 141, the furnace 145, the catalytic system 147 and additional water traps 143, are located downstream the chemical reactor 141 and upstream of the separation column 121. The chemical reactor 141 is connected in series in the branch connection 109.

In a variation, the treatment means 56 are located downstream of the separation column 121, between the separation column 121 and the detector 123.

The chemical reactor 141, comprises an entry opening 151, receives the untreated gas stream containing hydrocarbons to be analyzed and interfering compounds, and an exit opening 153 which distributes the treated gas stream containing substantially no interfering compound and substantially at least one of the hydrocarbons to be analyzed.

Inside the chemical reactor 141, a filter means 148 is inserted to immobilize and maintain the catalytic system 147.

This filter 148 is preferentially made of glass or ceramic or steel with a controlled porosity. The average size of the porosity network is chosen as a function of the size of the catalytic system, since its primary purpose is to retain the active phase (or catalytic phase) inside the chemical reactor.

For the treated gases, by "substantially no interfering compound" or by "the interfering compound substantially reacts", it is meant that each interfering compound has efficiently reacted in the chemical reactor in presence of the catalytic system 147, so that between 0 and 15 molar percent of interfering compounds remain in the outlet treated gaseous stream at the exit opening 153 relative to the content of interfering compounds in the inlet stream at the entry opening 151

For the treated gases, by "substantially at least one of the hydrocarbons to be analyzed" or by "without substantially reacting with at least one of the hydrocarbons to be analyzed", it is meant that more than 85 mole percent of at least one of the hydrocarbon to be analyzed available in the inlet untreated gas stream at the entry opening 151 is still present in the outlet treated gas stream at the exit opening 153.

Both the inlet untreated gas stream and the outlet treated gas stream are substantially in a gaseous phase, i.e. containing more than 90 volume percent of gas.

As indicated above, the catalytic system 147 is installed in the chemical reactor 141 to allow a contact with the gas stream circulating at a specific temperature. The catalytic system 147 typically comprises a catalyst support and a catalytic phase.

The catalytic support is for example a particulate solid surface where catalytic particles are deposited on. The catalytic support may be all type of ceramics, oxides or metallic alloys. As an example of oxides, the catalyst support could be quartz, alumina oxides, zirconium oxides, cerium oxides or all types of ionic conductors such as yttria-stabilized-zirconia or all type of mixed conductors.

The catalytic support can be in the form of a powder, honeycomb structures, macro-, micro-, or meso-porous solids, macro-porous grained solid, cellular materials, fibrous non-woven or woven material, foamed materials, simple porous pellets or all type of porous materials able to contain a catalytic phase. The catalytic materials can be presented as a thin film or coating deposited on adequate materials.

The catalytic phase is advantageously made of catalytic particles. It comprises for example a transition metal such as palladium, rhodium, iridium, platinum, ruthenium, gold, silver, cupper, tin, any metallic alloys such as Pt—Ru, or an association of metal particles such as Pt/Rh, or an association of at least one metal and an oxide such as titanium oxides, silver oxides, manganese oxides, vanadium oxides, copper oxides, strontium oxides, lanthanum oxides, or any association of oxides.

In a particular example, the catalytic system is composed of an aluminium oxide support having the chemical formula $Al_2O_3$. The support advantageously holds a catalyst formed by a dispersion of noble metal as such as platinum particles.

Advantageously, the catalytic system allows a selective oxidation reaction operating at a defined temperature range to be carried out to selectively oxidize at least one interfering compound without any substantial reaction of at least one hydrocarbon to be analyzed.

The oxidation reaction is run with the oxygen available in the untreated gas stream, and is called a selective catalytic reaction (SCR). The products of the reaction are carbon dioxide and water.

The temperature control unit 149 is located around the furnace 145. It is able to control the temperature of the gas stream circulating inside the chemical reactor 141 to maintain the reaction temperature at a defined range where at least one interfering compound substantially reacts, without any substantial reaction of at least one hydrocarbon to be analyzed.

The reaction products are collected in the collector 143 which is located downstream of the chemical reactor 141. In the particular example, water, which is one of the products resulting of the reaction, is trapped in the collector 143.

As a consequence, in the reactor 141 the interfering compounds are chemically transformed in another chemical substance which is either collected in the collector 143 or which does not interfere with the analysis of at least one of the hydrocarbons to be analyzed, carried out in the analyzer 55A.

As an example, when a hydrocarbon to be analyzed is methane ($CH_4$), and when an interfering compound is ethylene ($C_2H_4$), the predetermined temperature range for the selective catalytic oxidation of ethylene, without substantially oxidizing methane is between 50° C. and 450° C., in particular between 100° C. and 280° C. At this temperature, the ethylene substantially reacts with the oxygen present in the gas stream to form carbon dioxide ($CO_2$) and water ($H_2O$), whereas the methane does not substantially reacts with oxygen and remain unaffected.

The analysis method according to the invention, carried out during the operations of drilling a well, will now be described as an example, with reference to FIG. 1.

In order to carry out the drilling operations, the drilling tool 15 is driven in rotation by the surface installation 41.

A drilling fluid, advantageously a liquid, is introduced into the inner space 35 of the drill string 29 by the injection means 43.

The fluid moves downwards as far as the drilling head 27, and passes into the borehole through the drilling head 27.

The liquid cools and lubricates the drill string 29, and is especially used to evacuate from bottom to surface the cuttings generated during the drilling process. Indeed, the liquid collects the solid cuttings resulting from the drilling operation and moves back upwards through the annular space defined between the drill string 29 and the borehole 13. The liquid charged with solids, in particular cuttings or drilled rocks, is subsequently evacuated through the discharge pipe 25. It then forms the drilling mud charged with the gases to be analyzed.

These gases are then extracted and analyzed. With reference to FIG. 2, the peristaltic pump 61 is activated in order to sample continuously a given fraction of the drilling mud circulating in the pipe 25.

This mud fraction is conveyed to the enclosure 63 via the supply pipe 65, and is introduced into the enclosure.

The mud introduced into the enclosure 63 via the supply pipe 65 is evacuated by overflowing into the evacuation pipe 67 through the overflow passage 87. Furthermore, a portion of the evacuated mud temporarily resides in the siphon 93 of the evacuation pipe 67, which prevents any gases from entering the upper portion 75 of the enclosure 63 through the lower end 97 of the evacuation pipe 67. The introduction of gas into the enclosure 63 therefore takes place solely through the introduction inlet.

The agitator 79 is driven in rotation by the motor 81, and agitates the mud in the lower portion 73 of the enclosure 63 in order to carry out the continuous extraction of the gases contained in the mud. The mud gases extracted from the mud, which fill up the upper portion 75 are mixed with the carrier gas introduced through the injection passage 69.

As specified previously, an untreated gas stream of extracted gas is sampled continuously at the outlet 71 under the action of the suction caused by the pump 107. As specified above, the untreated stream of extracted gases is diluted in the carrier gas introduced through the injection port 69.

The gas stream contains different amounts of components, typically the $C_1$ to $C_n$ hydrocarbons to be analyzed in the analyser 55A, water vapour and interfering compounds such as ethylene, or alcohols, ethers, esters, ketones, or amines. These interfering compounds are present either because they are part of the composition of the mud located in the injection means 43, or because they result from chemical reactions between compounds constituting the mud when the mud circulates at the bottom of the well.

The untreated gas stream is then conveyed through the water trap 103 in order to eliminate the water vapour present by condensation. The gas stream then flows through the flow rate controller 105. The controlled flow rate of gas stream circulating in the line 54 is for example between 100 mL/min and 2000 mL/min.

Then, approximately less than 20% in volume of the gas stream may be sampled through the branch connection 109, whereas the remaining gas stream is transported to the atmosphere through the pump.

The untreated gas stream present in the branch connection 109 then circulates through the chemical treatment means 56.

In reference to FIG. 2, the untreated gas stream is introduced into the entry opening 151 of the chemical reactor 141.

The temperature control unit 149 is set at a defined temperature which is sufficient to carry out a substantial reaction of at least one of the interfering compounds, without substantial reaction of at least one of the hydrocarbons to be analyzed.

The untreated gas stream flows into the chemical reactor 141 and contacts the catalytic system 147, especially the catalytic phase.

In the reactor 141, the interfering compounds chemically react to be transformed into products which do not interfere with the measurement of at least one of the hydrocarbons to be analyzed.

The reaction is carried out on-line, directly on the gas stream which flows from the extractor to the analyzer, without sampling.

For example, when the interfering compound is an unsaturated hydrocarbon such as ethylene, the compound reacts with the oxygen available in the gas stream to produce carbon dioxide and water, when the temperature of the chemical reactor is maintained at a temperature lower than 400° C., and advantageously higher than 100° C.

At this temperature range, the interfering compounds are totally and ideally transformed in the chemical reactor 141.

The treated gas stream and the products resulting from the reaction of the interfering compounds are then evacuated through the exit opening 153.

The treated gas then flows to the collector 143 which collects the products of the reaction. In this example, the collector 143 is a water trap collecting the water produced by the selective catalytic oxidation in the chemical reactor 141.

The treated gas stream flowing continuously at the exit opening 153 of the treatment means 56 therefore contains the $C_1$ to $C_n$ hydrocarbons to be analyzed, but is free of at least one of the interfering compounds having an elution time of between the elution time of the first hydrocarbon to be analyzed and the elution time of the last hydrocarbon to be analysed in the separation column 121.

The treated gas stream is then introduced into the separation column 121, which permits the selective separation of the $C_1$ to $C_n$ hydrocarbons according to their elution time in the column 121.

The successive presence of these hydrocarbons is detected through the detector 123. A first detected peak corresponds to the $C_1$ hydrocarbon; a second peak corresponds to the $C_2$ hydrocarbon, a third peak to the $C_3$ hydrocarbon, a fourth peak to the $iC_4$ hydrocarbon, a fifth peak to the $nC_4$ hydrocarbon, a sixth peak to the $iC_5$ hydrocarbon and a seventh peak to the $nC_5$ hydrocarbon.

By way of comparison, when the untreated gas stream present upstream from the treatment means 56 in the branch connection 109 is injected directly into the column 121, without passing through the treatment means 56, the interfering compounds present in the untreated gas stream which have an elution time of between the elution time of the first hydrocarbon to be analyzed, namely the $C_1$ hydrocarbon, and the elution time of the last hydrocarbon to be analyzed, namely the $nC_5$ hydrocarbon, generate interfering peaks. These peaks mask, distort or disturb the normal peaks corresponding to certain of the hydrocarbons to be analyzed.

Carrying out the method according to the invention therefore makes it possible to measure on-line, at the outlet of an extractor, the presence of $C_1$ to $C_n$ hydrocarbons in the gas stream extracted from the mud and to quantify at least the $C_1$ to $C_5$ hydrocarbons precisely, without measurement skew caused by the presence of interfering compounds such as ethylene, or alcohol, ether or ester type.

The device 19 and the corresponding method are therefore simple to operate, in particular in a drilling installation. Maintenance of the device 19 for operating the device in an efficient manner is minimal, since the chemical reactor 141 can be operated continuously for an extended period of time.

Figure 3:
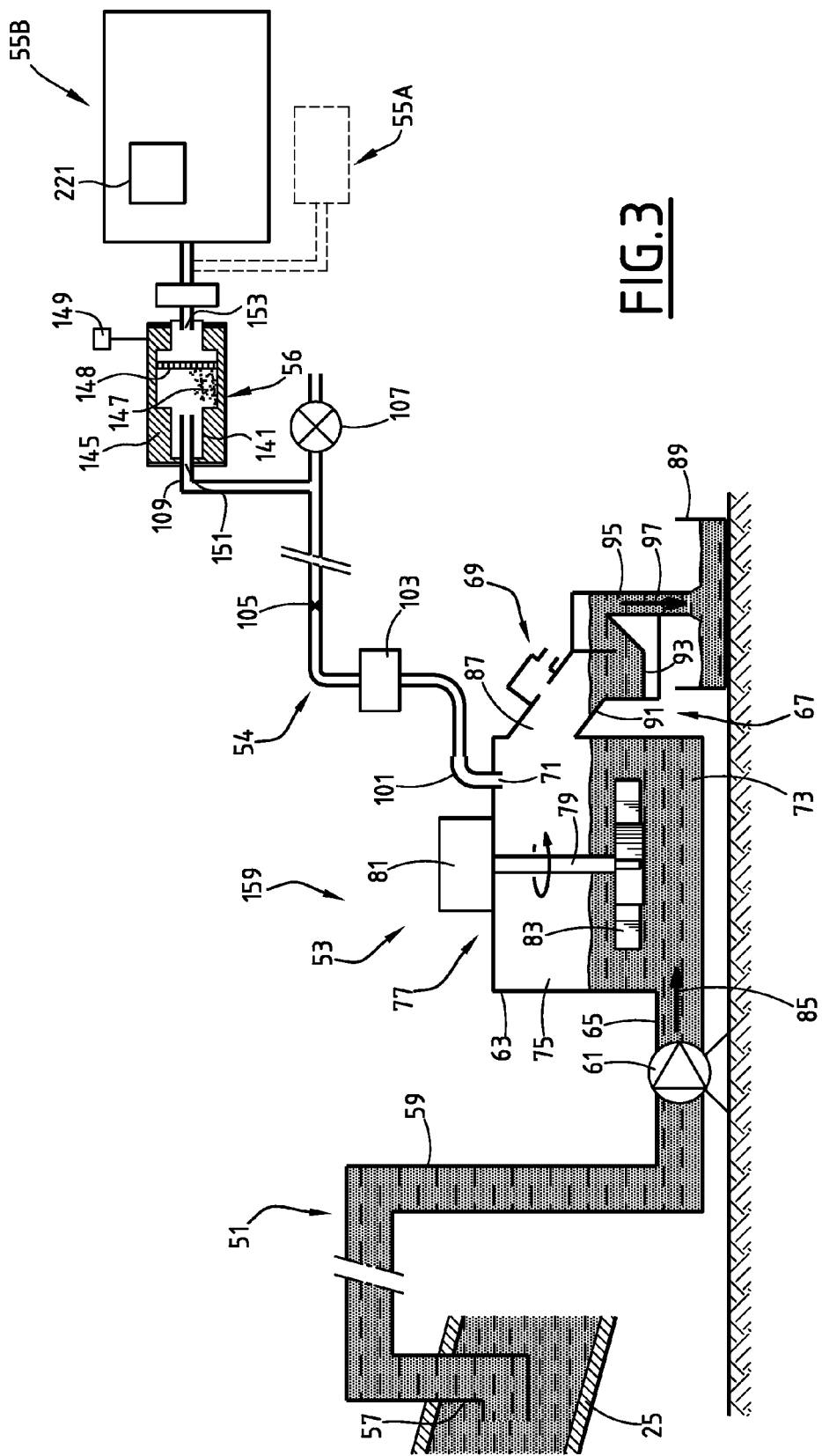
FIG. 3 is a similar view to FIG. 2 of a second analysis device according to the invention.

A second device 219 according to the invention is shown in FIG. 3.

The device shown in FIG. 3 is similar to the device 19 shown in FIG. 2. As a difference with the device 19, the analyzer 55B comprises an isotopic measurement unit 221, which is able to quantify the relative ratio of one particular isotope of a certain component to a second isotope of the same component.

In particular, the isotopic measurement unit 221 is able to quantify the $^{12}C/^{13}C$ isotopic ratio for at least one hydrocarbon, in particular for methane.

The isotopic measurement unit 221 for example comprises a separation column included e.g. in a gas chromatograph, advantageously similar to column 121, coupled with a detector formed by a mass spectrometer.

In a variant, the isotopic measurement device comprises an optical measurement detector such as disclosed in patent application WO 2009/037517 and WO 2008/017949 of the Applicant, with or without a separation column.

When the interfering compound is ethylene, the presence of ethylene in a gaseous stream to be analyzed skews the measurement of the isotopic ratio $^{12}C/^{13}C$ of the methane.

When using the second device 219 according to the invention, the selective catalytic oxidation of ethylene is continuously and substantially carried out in the chemical reactor 141 by the chemical treatment means 56, producing water and carbon dioxide. The water is trapped in the collector 143 and the measurement of the methane isotopic ratio is not skewed.

In a variation, shown in dotted lines in FIG. 3, a compositional analyzer 55A, identical to the one shown in FIG. 2 can also be added in parallel of the isotopic analyzer 55B to extend the chemical analysis.

The treated outlet gas stream, obtained at the outlet of the collector 143 is divided into two gaseous streams. A first stream flows to the compositional analyzer 55A and a second stream flows to the isotopic analyzer 55B.

Figure 4:
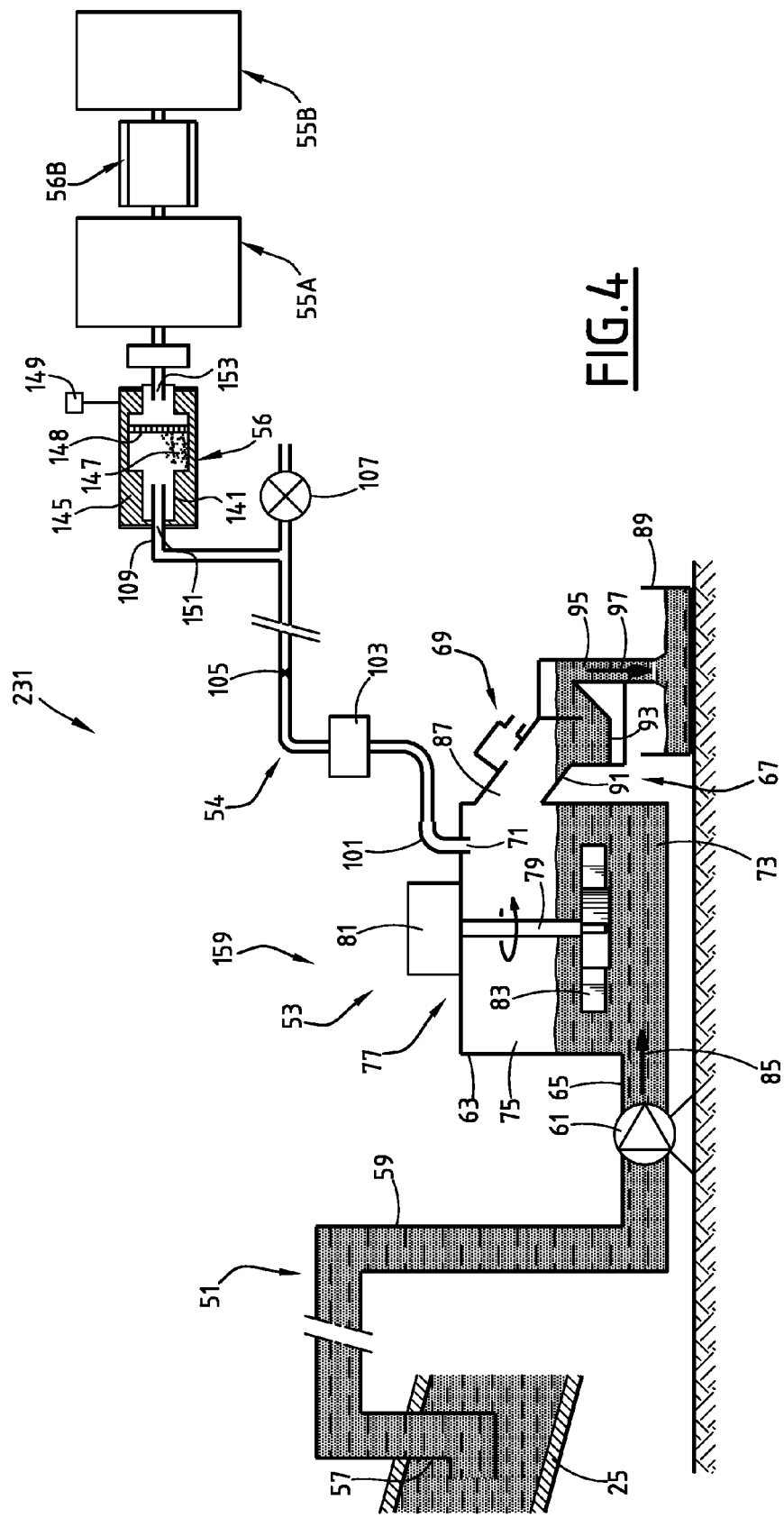
FIG. 4 is a similar view to FIG. 2 of a third analysis device according to the invention.

In the third device 231 shown in FIG. 4, the compositional analyzer 55A and the isotopic analyzer 55B are mounted in series. The position of the analyzer 55A is upstream the device 55B as illustrated in the FIG. 4, but it can also be the opposite depending of the type of measurement wanted.

In all cases, the treated gas passes successively into the two analyzers 55A and 55B. Between the two analyzers, additional treatment means 56B similar to as the treatment means 56 can be placed to increase and widen the chemical treatment of the gases before analysis. The additional treatment means 56B are used to substantially carry out the reaction with at least one interfering compound without substantial reaction of at least one hydrocarbon to be analyzed in the same proportion defined above for treatment means 56.

In one variant, the extractor 53 is formed by a hollow pipe immersed in the mud and having a porous wall forming an extraction membrane for the gases contained in the mud. The hollow pipe is connected to an analyser 55A, 55B by another short length pipe.

The treatment means 56 described previously are placed between the extraction membrane and the detector of the analyser 55A, 55B.

In another realisation, the treatment means 56 can work at room temperature by adapting an UV light system. The furnace 145 may be omitted.

For example, the selective catalytic reaction can be performed in the chemical reactor 141 with a photo-catalytic system. In this case, the reaction is a photo-oxidation. The chemical reactor is then associated either with a temperature control unit or/and a UV light control unit depending of the type of desired selective catalytic reaction.

Thus, the catalytic system 147 is adapted in accordance with the equipment used. For example, to carry out a photo-oxidation, the catalytic phase is preferentially titanium oxides.

The invention claimed is:

1. A device for analyzing at least one hydrocarbon contained in a drilling fluid, comprising:
    an extractor for continuously extracting gases contained in the drilling fluid, the extractor having an outlet at which the gas stream is sampled, the gas stream containing at least one hydrocarbon to be analyzed and at least one interfering compound;
    a transport line, connected to the outlet of the extractor to transport the gas stream;
    an analyzer comprising a detector able to measure the hydrocarbons to be analyzed in the gas stream; and
    a chemical reactor located between the extractor and the detector and receiving at least part of the gas stream, the chemical reactor being able to carry out a selective catalytic reaction of at least one interfering compound present in the gas stream without any substantial reaction of at least one of the hydrocarbons to be analyzed, wherein the at least one interfering compound comprises ethylene (C2H4), wherein the chemical reactor contains a catalytic system having a catalyst dispersed on a support;
    wherein the catalyst comprises at least a transition metal, wherein the transition metal comprise at least one of platinum, rhodium or palladium.

2. The device according to claim 1, further comprising a temperature control unit to control the temperature of the selective catalytic reaction of the at least one interfering compound in the chemical reactor.

3. The device according to claim 1, wherein the chemical reactor comprises a UV light unit able to carry out a selective photo-oxidation of the at least one interfering compound.

4. The device of claim 1, further comprising a separation column able to separate a plurality of hydrocarbons to be analyzed according to their elution time in the separation column, the separation column being placed between the extractor and the detector, upstream or downstream of the chemical reactor.

5. The device of claim 1, wherein the analyzer comprises a compositional analysis unit, comprising calculation means suitable for qualifying and/or quantifying each hydrocarbon to be analyzed.

6. The device of claim 1, wherein the analyzer comprises an isotopic measurement unit.

7. A method for analyzing at least one hydrocarbon contained in a drilling fluid, comprising the following steps:
continuously extracting a gas stream of gases contained in the drilling fluid within an extractor,
at an outlet of the extractor, sampling the gas stream where at least one hydrocarbon to be analyzed and at least one interfering compound are present;
collecting and transporting the gas stream through a transport line connected to the outlet of the extractor;
measuring at least one of the hydrocarbons to be analyzed in the gas stream in an analyzer comprising a detector;
passing at least part of the gas stream through a chemical reactor located between the extractor and the detector;
carrying out a selective catalytic reaction of at least one of the interfering compounds in the chemical reactor, without any substantial reaction of at least one of the hydrocarbons to be analyzed, wherein the at least one interfering compound comprises ethylene (C2H4), wherein the chemical reactor contains a catalytic system-having a catalyst dispersed on a support and wherein the catalyst comprises at least a transition metal, wherein the transition metal comprise at least one of platinum, rhodium or palladium.

8. The method according to claim 7, wherein the selective reaction step comprises substantially reacting at least 85 molar percent of the interfering compounds, without substantially reacting at least 85 molar percent of the hydrocarbon to be analyzed.

9. The method according to claims 7, wherein the selective reaction step comprises controlling the temperature of the chemical reactor in a temperature range where at least one of the interfering compounds selectively reacts, without any substantial reaction of at least one of the hydrocarbons to be analyzed.

10. The method according to claim 7, wherein the selective reaction step comprises selectively oxidizing, in particular photo-oxidizing, at least one of the interfering compounds in the chemical reactor without substantially oxidizing at least one of the hydrocarbons to be analyzed.

11. Method according to claim 7 further comprising a step of passing the gas stream into a separation column connected to the transport line in order to separate a plurality of hydrocarbons to be analyzed according to their elution time in the separation column.

12. The method according to claim 7 wherein the analyzing step comprises qualifying and/or quantifying each hydrocarbons to be analyzed.

13. The method according to claim 7 wherein the analyzing step comprises the determination of the isotopic content of at least one of the hydrocarbons to be analyzed.

14. A device for analyzing at least one hydrocarbon contained in a drilling fluid, comprising:
an extractor for continuously extracting gases contained in the drilling fluid, the extractor having an outlet at which the gas stream is sampled, the gas stream containing at least one hydrocarbon to be analyzed and at least one interfering compound;
a transport line, connected to the outlet of the extractor to transport the gas stream;
an analyzer comprising a detector able to measure the hydrocarbons to be analyzed in the gas stream; and
a chemical reactor located between the extractor and the detector and receiving at least part of the gas stream, the chemical reactor being able to carry out a selective catalytic reaction of at least one interfering compound present in the gas stream without any substantial reaction of at least one of the hydrocarbons to be analyzed, wherein the at least one interfering compound comprises ethylene (C2H4), and the chemical reactor comprising a UV light unit able to carry out a selective photo-oxidation of the at least one interfering compound;
wherein the chemical reactor contains a catalytic system having a catalyst dispersed on a support.

15. The device of claim 14, wherein the catalytic system comprises at least a transition metal, wherein the transition metal comprise at least one of platinum, rhodium or palladium.

16. The device of claim 14, further comprising a separation column, able to separate a plurality of hydrocarbons to be analyzed according to their elution time in the separation column, the separation column being placed between the extractor and the detector, upstream or downstream of the chemical reactor.

17. The device of claim 14, wherein the analyzer comprises a compositional analysis unit, comprising calculation means suitable for qualifying and/or quantifying each hydrocarbon to be analyzed.

18. The device of claim 14, wherein the analyzer comprises an isotopic measurement unit.

19. The device of claim 1 or 14, wherein the catalyst comprise platinum particles and the support comprises an oxide.

* * * * *